US012773480B2

(12) United States Patent
Nakai et al.

(10) Patent No.: US 12,773,480 B2
(45) Date of Patent: Oct. 27, 2026

(54) FLEXIBLE TUBE FOR ENDOSCOPE, ENDOSCOPIC MEDICAL DEVICE, AND METHODS FOR PRODUCING THE SAME

(71) Applicant: FUJIFILM Corporation, Tokyo (JP)

(72) Inventors: Yoshihiro Nakai, Kanagawa (JP); Kazushi Furukawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 667 days.

(21) Appl. No.: 18/147,338

(22) Filed: Dec. 28, 2022

(65) Prior Publication Data

US 2023/0139268 A1 May 4, 2023

Related U.S. Application Data

(63) Continuation of application No. PCT/JP2021/024360, filed on Jun. 28, 2021.

(30) Foreign Application Priority Data

Jun. 29, 2020 (JP) ................................ 2020-111754

(51) Int. Cl.
*A61L 29/08* (2006.01)

(52) U.S. Cl.
CPC ......... *A61L 29/085* (2013.01); *A61L 2420/02* (2013.01)

(58) Field of Classification Search
CPC .... A61L 29/085; A61L 2420/02; A61L 29/06; A61B 1/005; C08K 5/09; C08K 5/16; C08L 63/00; C08L 67/00; C08L 79/00
See application file for complete search history.

(56) References Cited

U.S. PATENT DOCUMENTS

2009/0198021 A1 8/2009 Ogura et al.
2010/0280319 A1 11/2010 Ogura et al.
(Continued)

FOREIGN PATENT DOCUMENTS

CN 101502679 A 8/2009
CN 105074306 A 11/2015
(Continued)

OTHER PUBLICATIONS

International Search Report issued Sep. 7, 2021 in International Application No. PCT/JP2021/024360.
(Continued)

*Primary Examiner* — James C Yager
(74) *Attorney, Agent, or Firm* — Sughrue Mion, PLLC

(57) ABSTRACT

Provided are a flexible tube for an endoscope, the flexible tube having a sleeve-shaped flexible-tube base having flexibility and a cover layer covering an outer periphery of the flexible-tube base, in which the cover layer includes a chain-extended product of a polyester having a naphthalene structure, and the chain-extended product includes a constituent component derived from at least one chain extender selected from the group consisting of (A) an epoxy compound, (B) an isocyanate compound, (C) an amine compound, (D) an oxazoline compound, (E) a carbodiimide compound having a molecular weight of less than 3,000, and (F) a carboxylic anhydride and a constituent component derived from a polyester having a naphthalene structure, an endoscopic medical device using the flexible tube, a method for producing the flexible tube for an endoscope, and a method for producing the endoscopic medical device.

7 Claims, 2 Drawing Sheets

(56) References Cited

U.S. PATENT DOCUMENTS

| | | | |
|---|---|---|---|
| 2016/0024343 A1 | 1/2016 | Nakai et al. |
| 2020/0100646 A1 | 4/2020 | Furukawa et al. |
| 2020/0405918 A1 | 12/2020 | Nakai et al. |
| 2022/0119675 A1 | 4/2022 | Nakai et al. |

FOREIGN PATENT DOCUMENTS

| | | | | |
|---|---|---|---|---|
| CN | 110709000 A | 1/2020 | | |
| JP | 2004-141487 A | 5/2004 | | |
| JP | 2008-540786 A | 11/2008 | | |
| JP | 2009-183467 A | 8/2009 | | |
| JP | 2010-189598 A | 9/2010 | | |
| JP | 2014-188217 A | 10/2014 | | |
| JP | 2016-209649 A | 12/2016 | | |
| WO | WO-2006122896 A1 * | 11/2006 | ............... | D01F 6/62 |
| WO | 2014/157375 A1 | 10/2014 | | |
| WO | 2019/004473 A1 | 1/2019 | | |
| WO | 2019/189035 A1 | 10/2019 | | |

OTHER PUBLICATIONS

Written Opinion issued Sep. 7, 2021 in International Application No. PCT/JP2021/024360.

International Preliminary Report on Patentability dated Dec. 13, 2022 with a Translation of the Written Opinion of the International Searching Authority in Application No. PCT/JP2021/024360.

Office Action issued Sep. 26, 2023 in corresponding Japanese Application No. 2022-533994.

Office Action issued Dec. 26, 2023 in Japanese Application No. 2022-533994.

Chinese Office Action dated Jul. 9, 2025 in Application No. 202180043576.4.

Office Action issued Dec. 12, 2025 in Chinese Patent Application No. 202180043576.4.

* cited by examiner

FLEXIBLE TUBE FOR ENDOSCOPE, ENDOSCOPIC MEDICAL DEVICE, AND METHODS FOR PRODUCING THE SAME

CROSS-REFERENCE TO RELATED APPLICATIONS

This application is a Continuation of PCT International Application No. PCT/JP2021/024360 filed on Jun. 28, 2021, which claims priority under 35 U.S.C. § 119 (a) to Japanese Patent Application No. 2020-111754 filed in Japan on Jun. 29, 2020. Each of the above applications is hereby expressly incorporated by reference, in its entirety, into the present application.

BACKGROUND OF THE INVENTION

1. Field of the Invention

The present invention relates to a flexible tube for an endoscope, an endoscopic medical device, and methods for producing the same.

2. Description of the Related Art

Endoscopes are medical devices for examining the inside of the body cavity, the inside of the digestive tract, the esophagus, or the like of a patient. Since endoscopes are inserted and used in the body, it is desirable to provide endoscopes that do not damage organs or cause pain or discomfort to a patient. In view of such a requirement, a spiral tube formed by spirally winding a soft, bendable metal strip is adopted as a flexible tube that forms an insertion section of an endoscope. Furthermore, the periphery of the spiral tube is covered with a flexible resin so that the spiral tube does not cause stimulation, damage, or the like to the inner surface of, for example, the esophagus, digestive tract, or body cavity.

Endoscopes for examining the inside of the human body are repeatedly used. The flexible tube that forms the insertion section of an endoscope needs to be washed and disinfected with a chemical each time it is used. In particular, when the flexible tube is inserted into a highly susceptible region, such as the bronchus, cleanliness at a level of sterilization higher than disinfection is required. Accordingly, a flexible tube for an endoscope is required to have high durability enough to withstand repeated sterilization treatment.

For example, JP2009-183467A describes a flexible tube for an endoscope, the flexible tube being covered with an outer cover formed of an elastomer molded body for an endoscope obtained by crosslinking two or more thermoplastic polyester elastomers. This flexible tube is reported to be unlikely to undergo degradation of the outer cover due to various chemicals.

JP2014-188217A describes a flexible tube for an endoscope, the flexible tube being covered with an outer cover constituted by two layers, namely, a resin layer including one or more elastomers or chain-extended products thereof selected from the group consisting of polyester elastomers, polyurethane elastomers, and polyamide elastomers and a resin layer including chain-extended products of two or more elastomers selected from the group consisting of polyester elastomers, polyurethane elastomers, and polyamide elastomers. This flexible tube is reported to have good peracetic acid resistance.

JP2004-141487A describes a flexible tube for an endoscope, the flexible tube being formed by covering a surface of a flexible-tube base material with an outer cover, in which polybutylene naphthalate is used as a hard segment of a polyester elastomer constituting the outer cover, and discloses that, with this configuration, degradation of the outer cover due to a washing solution or a disinfecting solution can be suppressed, and durability to sterilization treatment using an autoclave can also be improved.

JP2010-189598A discloses that a thermoplastic resin composition containing a resin having polybutylene succinate chain and one or more copolymer resins selected from the group consisting of aliphatic ether-ester copolymer resins and aliphatic ether-amide copolymer resins has good heat resistance for sterilization at high temperature, and that a tube of a flexible tube for an endoscope is formed using this composition.

WO2019/189035A discloses that a thermoplastic resin having a 10% tensile strength of 10 MPa or more is used as a constituent material of a resin layer covering a flexible-tube base, and a hindered amine compound having a molecular weight of 500 or more is mixed with the resin, and discloses that, with this configuration, degradation of the resin layer is unlikely to occur even when hydrogen peroxide plasma treatment is repeated or a hydrogen peroxide gas treatment is repeated.

SUMMARY OF THE INVENTION

With regard to sterilization durability of a flexible tube for an endoscope, in recent years, chemical sterilization treatment using hydrogen peroxide plasma, hydrogen peroxide gas, or the like has also been widely performed instead of autoclave treatment from the viewpoint of suppressing hygrothermal aging of the flexible tube for an endoscope. Furthermore, recently, sterilization treatment using ozone water in which a very small amount of ozone ($O_3$) is dissolved in water has been performed. This ozone water produces strong active species such as hydroxy radicals, and the oxidizing power thereof is stronger than that of hydrogen peroxide gas. Accordingly, substantially only fluororesins are known as organic materials that can withstand the sterilization treatment with ozone water.

In order to allow an endoscope insertion section to reach an affected part or the like smoothly and reliably, the endoscope insertion section is repeatedly bent. Therefore, the endoscope insertion section is required to have a characteristic (bending durability) that a flexible-tube base and a cover layer for this flexible-tube base are unlikely to peel off even when the insertion section is repeatedly bent, and that cracking or the like is unlikely to occur in the cover layer.

In order to insert an endoscope insertion section into the body without giving discomfort to a patient and to allow the insertion section to reach an affected part or the like smoothly and reliably, the flexible tube for an endoscope is required not only to have improved bending durability but also to have a smooth surface without irregularities and good slidability with the inner surface of the body cavity, the digestive tract, the esophagus, or the like, that is, to have good surface smoothness.

In view of the above points, an object of the present invention is to provide a flexible tube for an endoscope, the flexible tube exhibiting good sterilization durability against strong sterilization treatment using, for example, ozone water and having good bending durability and surface smoothness, and an endoscopic medical device using the flexible tube. Another object of the present invention is to provide a method for producing the flexible tube for an endoscope and a method for producing the endoscopic medical device.

As a result of extensive studies in view of the above-described problems, the inventors of the present invention have found that the above problems can be solved by using, as a constituent material of a cover layer (outer cover) that forms a flexible tube for an endoscope, a polyester which has a constituent component derived from a specific chain extender and in which a naphthalene structure is introduced, in the cover layer for the flexible tube for an endoscope. This finding has led to the completion of the present invention.

The above objects have been achieved by the following means.

<1>

A flexible tube for an endoscope, the flexible tube having a sleeve-shaped flexible-tube base having flexibility; and a cover layer covering an outer periphery of the flexible-tube base, wherein the cover layer includes a chain-extended product of a polyester having a naphthalene structure, and the chain-extended product includes a constituent component derived from at least one chain extender selected from the group consisting of (A) an epoxy compound, (B) an isocyanate compound, (C) an amine compound, (D) an oxazoline compound, (E) a carbodiimide compound having a molecular weight of less than 3,000, and (F) a carboxylic anhydride and a constituent component derived from a polyester having a naphthalene structure.

<2>

The flexible tube for an endoscope according to <1>, wherein the chain-extended product of a polyester having a naphthalene structure includes a constituent component derived from the (A) epoxy compound, and the constituent component derived from the (A) epoxy compound includes a constituent component derived from a bifunctional to hexafunctional epoxy compound.

<3>

The flexible tube for an endoscope according to <1> or <2>, wherein the chain-extended product of a polyester having a naphthalene structure includes a constituent component derived from the (B) isocyanate compound, and the constituent component derived from the (B) isocyanate compound includes a constituent component derived from a bifunctional or trifunctional isocyanate compound.

<4>

The flexible tube for an endoscope according to any one of <1> to <3>, wherein the chain-extended product of a polyester having a naphthalene structure includes a constituent component derived from the (C)amine compound, and the constituent component derived from the (C)amine compound includes a constituent component derived from a bifunctional to tetrafunctional amine compound.

<5>

The flexible tube for an endoscope according to any one of <1> to <4>, wherein the chain-extended product of a polyester having a naphthalene structure includes a constituent component derived from the (D) oxazoline compound, and the constituent component derived from the (D) oxazoline compound includes a constituent component derived from a polymeric oxazoline compound.

<6>

The flexible tube for an endoscope according to any one of <1> to <5>, wherein the chain-extended product of a polyester having a naphthalene structure includes a constituent component derived from the (E) carbodiimide compound having a molecular weight of less than 3,000, and the constituent component derived from the (E) carbodiimide compound having a molecular weight of less than 3,000 includes a constituent component derived from a carbodiimide compound having a ring structure.

<7>

The flexible tube for an endoscope according to any one of <1> to <6>, wherein the chain-extended product of a polyester having a naphthalene structure includes a constituent component derived from the (F) carboxylic anhydride, and the constituent component derived from the (F) carboxylic anhydride includes a constituent component derived from a tetracarboxylic dianhydride.

<8>

An endoscopic medical device having the flexible tube for an endoscope according to any one of <1> to <7>.

<9>

A method for producing a flexible tube for an endoscope, the method including forming a cover layer on at least an outer periphery of a sleeve-shaped flexible-tube base having flexibility using a cover layer-forming material that includes at least one chain extender selected from the group consisting of (A) an epoxy compound, (B) an isocyanate compound, (C) an amine compound, (D) an oxazoline compound, (E) a carbodiimide compound having a molecular weight of less than 3,000, and (F) a carboxylic anhydride and a polyester having a naphthalene structure.

<10>

A method for producing an endoscopic medical device, the method including a step of obtaining a flexible tube for an endoscope by the method for producing a flexible tube for an endoscope according to <9>; and a step of incorporating the obtained flexible tube for an endoscope into an insertion section of an endoscopic medical device.

<11>

A method for producing an endoscopic medical device, the method including incorporating the flexible tube for an endoscope according to any one of <1> to <7> into an insertion section of an endoscopic medical device.

In the present specification, if it is not explicitly specified whether a compound is substituted or unsubstituted, it is meant that the compound may have any substituent within the range in which the desired effect is achieved.

In the present specification, when the number of carbon atoms of a group is specified, the number of carbon atoms means the number of carbon atoms of the whole group. That is, when this group is in a form further having a substituent, the number of carbon atoms means the number of carbon atoms of the whole that includes this substituent.

In the present specification, a numerical range represented using "to" mean a range that includes a numerical value before "to" as a lower limit and a numerical value after "to" as an upper limit.

The flexible tube for an endoscope according to the present invention exhibits good sterilization durability against strong sterilization treatment using, for example, ozone water and has good bending durability and surface smoothness. The endoscopic medical device according to the present invention is a device that includes the flexible tube for an endoscope, the flexible tube having the above good characteristics. The method for producing a flexible tube for an endoscope according to the present invention enables the production of the flexible tube for an endoscope according to the present invention, the flexible tube having the above characteristics. The method for producing an endoscopic medical device according to the present invention enables the production of an endoscopic medical device that includes the flexible tube for an endoscope according to the present invention, the flexible tube having the above characteristics.

DESCRIPTION OF THE PREFERRED EMBODIMENTS

Flexible Tube for Endoscope

Figure 1:
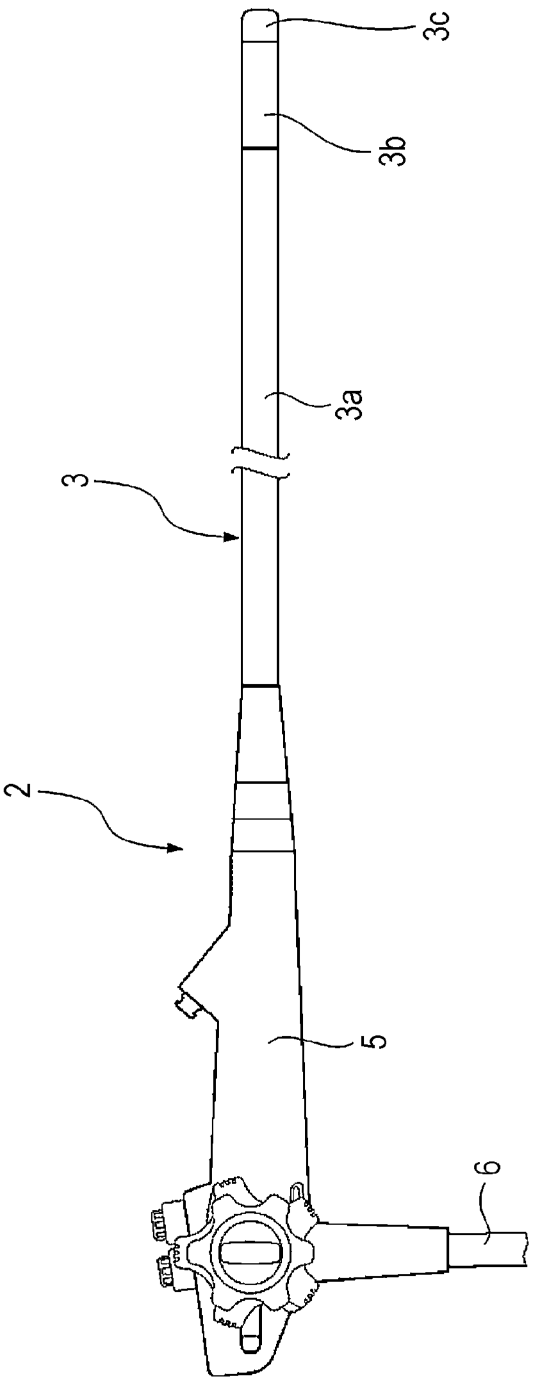
FIG. 1 is an external view illustrating a configuration of an electronic endoscope.

A flexible tube for an endoscope (hereinafter, the flexible tube for an endoscope may be simply referred to as a "flexible tube") according to the present invention is a flexible tube for an endoscope, the flexible tube having a sleeve-shaped flexible-tube base having flexibility, and a cover layer covering an outer periphery of the flexible-tube base. The cover layer includes a chain-extended product of a polyester having a naphthalene structure.

The chain-extended product of a polyester having a naphthalene structure is a polymer obtained by subjecting a polyester having a naphthalene structure to chain extension treatment using at least one chain extender selected from the group consisting of (A) an epoxy compound, (B) an isocyanate compound, (C) an amine compound, (D) an oxazoline compound, (E) a carbodiimide compound having a molecular weight of less than 3,000, and (F) a carboxylic anhydride. That is, the chain-extended product of a polyester having a naphthalene structure includes a constituent component derived from at least one chain extender selected from the group consisting of (A) an epoxy compound, (B) an isocyanate compound, (C) an amine compound, (D) an oxazoline compound, (E) a carbodiimide compound having a molecular weight of less than 3,000, and (F) a carboxylic anhydride and a constituent component derived from a polyester having a naphthalene structure.

The flexible tube according to the present invention exhibits good sterilization durability against strong sterilization treatment using, for example, ozone water, and has good bending durability and good surface smoothness. That is, the polyester having a naphthalene structure is considered to exhibit a barrier function of inhibiting migration and permeation of active species having sterilizing activity, such as hydroxy radicals, into the cover layer due to a large molecular area of the naphthalene structure, and the barrier function is considered to be effectively enhanced by converting the polyester having such a structure into a chain-extended product (crosslinked product) using a specific chain extender in the present invention. Furthermore, it is considered that the naphthalene structure of the chain-extended product in the cover layer also inhibits migration of the unreacted chain extender to the surface of the cover layer at the time of molding under heating, and an appropriate crosslink density and a high molecular weight are realized by forming the chain-extended product, thereby improving characteristics required for an endoscope, such as surface smoothness, flexibility, and fatigue resistance.

Cover Layer

The flexible tube according to the present invention has a cover layer on an outer periphery of a flexible-tube base. The flexible tube according to the present invention may have an interlayer on the flexible-tube base, and in this case, the flexible tube according to the present invention has a covering layer on the interlayer.

In the present invention, the cover layer may be formed of a single layer or a multilayer structure including two or more layers and is preferably formed of a single layer. In the present invention, when the cover layer is formed of a single layer, the single-layer cover layer includes a chain-extended product of a polyester having a naphthalene structure. When the cover layer is formed of a multilayer structure including two or more layers, at least the outermost layer includes a chain-extended product of a polyester having a naphthalene structure. That is, the cover layer in the present invention includes, in the outermost layer thereof, a chain-extended product of a polyester having a naphthalene structure.

Polyester Having Naphthalene Structure

Examples of the polyester having a naphthalene structure include polyester resins having a naphthalene structure and polyester elastomers having a naphthalene structure.

The polyester having a naphthalene structure is preferably a polyester composed of a dicarboxylic acid component (a constituent component derived from a dicarboxylic acid) including a naphthalenedicarboxylic acid component (a constituent component derived from naphthalenedicarboxylic acid) and a diol component (a constituent component derived from a diol).

A specific example of the dicarboxylic acid component that is preferred as the naphthalenedicarboxylic acid component is 2,6-naphthalenedicarboxylic acid component.

First, a polyester resin having a naphthalene structure will be described.

The polyester resin having a naphthalene structure preferably has a naphthalenedicarboxylic acid component. The polyester resin having a naphthalenedicarboxylic acid component may have, as the dicarboxylic acid component, a dicarboxylic acid component other than the naphthalenedicarboxylic acid component.

The dicarboxylic acid component other than the naphthalenedicarboxylic acid component is not particularly limited, and those typically used as a dicarboxylic acid component constituting a polyester resin can be widely applied. Examples thereof include constituent components derived from terephthalic acid, isophthalic acid, phthalic acid (orthophthalic acid), 5-sodium sulfoisophthalic acid, oxalic acid, succinic acid, adipic acid, sebacic acid, azelaic acid, dodecanedioic acid, dimer acid, maleic acid, fumaric acid, itaconic acid, citraconic acid, mesaconic acid, cyclohexanedicarboxylic acid, and the like. One or two or more of these dicarboxylic acid components can be used.

In the polyester resin having a naphthalene structure, diol components typically used as a diol component constituting a polyester resin can be widely applied. Examples thereof include constituent components derived from ethylene glycol, diethylene glycol, 1,3-propanediol, 1,4-butanediol, neopentyl glycol, 1,6-hexanediol, cyclohexane dimethanol, triethylene glycol, bisphenol A, bisphenol S, and the like. One or two or more of these diol components can be used.

The polyester resin having a naphthalene structure may contain a hydroxycarboxylic acid component as a constituent component. Examples of the hydroxycarboxylic acid component include constituent components derived from ε-caprolactone, lactic acid, 4-hydroxybenzoic acid, and the like. One or two or more of these hydroxycarboxylic acid components are used.

The polyester resin having a naphthalene structure may be a homopolymer or copolymer composed of the above-described components and may further contain a small amount of a trifunctional compound component such as trimellitic acid, trimesic acid, pyromellitic acid, trimethylolpropane, glycerin, or pentaerythritol.

As the polyester resin having a naphthalene structure, two or more homopolymers or copolymers composed of the above components may be used in combination.

Next, a polyester elastomer having a naphthalene structure will be described.

The polyester elastomer having a naphthalene structure preferably has a naphthalenedicarboxylic acid component. More preferably, the polyester elastomer having a naphthalene structure is a copolymer that contains a hard segment composed of a crystalline polyester chain containing, as constituent components, a dicarboxylic acid component including a naphthalenedicarboxylic acid component and a low-molecular-weight diol component and at least one soft segment selected from the group consisting of (i) to (iii) below.

(i) An amorphous soft segment composed of an aliphatic polyester chain
(ii) An amorphous soft segment composed of an aliphatic polymer diol component
(iii) A soft segment composed of a polyester chain containing an aliphatic polymer diol component and a dicarboxylic acid component including an aromatic dicarboxylic acid That is, the naphthalene structure may be introduced in either one or both of the hard segment and the soft segment and is preferably introduced in at least the hard segment.

A specific example of the dicarboxylic acid component that is preferred as the naphthalenedicarboxylic acid component is 2,6-naphthalenedicarboxylic acid component. A polyester elastomer containing a hard segment having a naphthalene structure will be described below.

In the polyester elastomer containing a hard segment having a naphthalene structure, the hard segment preferably has a naphthalenedicarboxylic acid component. When the hard segment has a naphthalenedicarboxylic acid component, all of the dicarboxylic acid components of the hard segment may be the naphthalenedicarboxylic acid component, or the hard segment may have a dicarboxylic acid component other than the naphthalenedicarboxylic acid component. As the dicarboxylic acid component that is other than the naphthalenedicarboxylic acid component and that constitutes the hard segment, those typically used as a dicarboxylic acid component constituting a hard segment of a typical polyester elastomer can be widely applied. Examples thereof include the dicarboxylic acid components that are other than the naphthalenedicarboxylic acid component and described in the description of the polyester resin having a naphthalene structure. The hard segment can have one or two or more of the dicarboxylic acid components. In particular, the dicarboxylic acid component that is other than the naphthalenedicarboxylic acid component and that constitutes the hard segment preferably includes an aromatic dicarboxylic acid component (dicarboxylic acid component having an aromatic ring). The aromatic dicarboxylic acid component preferably accounts for 50% by mass or more (preferably 70% by mass or more, more preferably 80% by mass or more, and more preferably 90% by mass or more) of the dicarboxylic acid component other than the naphthalenedicarboxylic acid component. It is also preferred that all of the dicarboxylic acid components that are other than the naphthalenedicarboxylic acid component and that constitute the hard segment be aromatic dicarboxylic acid components.

As the diol component constituting the hard segment, those typically used as a diol component constituting a polyester resin can be widely applied. Examples thereof include the diol components described in the polyester resin having a naphthalene structure. The hard segment can have one or two or more of the diol components.

The hard segment may have, as a constituent component, one or two or more of the hydroxycarboxylic acid components described in the description of the polyester resin having a naphthalene structure.

The hard segment may be a homopolymer or copolymer composed of the constituent components described above.

When the soft segment is the (i) aliphatic polyester chain, the dicarboxylic acid component constituting the aliphatic polyester chain is not particularly limited as long as the dicarboxylic acid component is an aliphatic dicarboxylic acid component. The aliphatic polyester chain can have a constituent component derived from, for example, oxalic acid, succinic acid, adipic acid, sebacic acid, azelaic acid, dodecanedioic acid, dimer acid, maleic acid, fumaric acid, itaconic acid, citraconic acid, mesaconic acid, cyclohexanedicarboxylic acid, or the like. The aliphatic polyester chain can have one or two or more of these dicarboxylic acid components.

The diol component of the aliphatic polyester chain constituting the soft segment is not particularly limited as long the diol component is an aliphatic diol component. Examples thereof include aliphatic diol components derived from ethylene glycol, diethylene glycol, triethylene glycol, propylene glycol, dipropylene glycol, 3-methyl-1,5-pentanediol, 1,3-propanediol, 1,4-butanediol, 1,9-nonanediol, neopentyl glycol, 1,5-pentanediol, 1,6-hexanediol, decamethylene glycol, cyclohexane dimethanol, and the like. The aliphatic polyester chain can have one or two or more of these diol components. It is also preferred that the aliphatic polyester chain have an aliphatic polymer diol component as the diol component. Examples of the aliphatic polymer diol component include polyalkylene glycols such as polyethylene glycol, polypropylene glycol, and polytetramethylene glycol. The aliphatic polyester chain can have one or two or more of these aliphatic polymer diol components. In the present invention, the polyalkylene glycols refer to compounds represented by $HO—[(CH_2)_mO]_n—H$. Here, m is preferably 1 to 12, more preferably 2 to 10, still more preferably 2 to 8, and even more preferably 2 to 6. n is preferably 5 to 100, and more preferably 10 to 50.

When the soft segment is the (ii) amorphous soft segment derived from an aliphatic polymer diol, the aliphatic polymer diol is not particularly limited as long as it is an aliphatic polymer diol. Examples thereof include polyalkylene glycols such as polyethylene glycol, polypropylene glycol, and polytetramethylene glycol. The polyester elastomer can have a structure having, as the soft segment, an aliphatic polymer diol component derived from one or two or more of these. The structures of the polyalkylene glycols are as described above.

When the soft segment is the (iii) soft segment composed of a polyester chain containing an aliphatic polymer diol component and a dicarboxylic acid component including an aromatic dicarboxylic acid, the aliphatic polymer diol component is not particularly limited, and examples thereof include constituent components derived from the aliphatic polymer diols described in (ii) above. Examples of the aromatic dicarboxylic acid component include constituent components derived from naphthalenedicarboxylic acids. When the polyester chain includes a dicarboxylic acid component other than the aromatic dicarboxylic acid component, examples of the dicarboxylic acid component include the dicarboxylic acid components described in (i) above.

Since the polyester having a naphthalene structure reacts with a chain extender to form a chain-extended product, the polyester has a functional group that reacts with a functional group of the chain extender, for example, at least one of a hydroxy group or a carboxy group, or at least one of these groups is formed by kneading under heating during the reaction. The polyester has these functional groups in at least one of the main chain or a side chain of the polymer, and preferably has these functional groups at one terminal or both terminals of the main chain. These functional groups can be introduced into the polyester, for example, by appropriately selecting the raw materials used in the synthesis of the polyester, or can also be introduced into the polyester by adjusting the conditions for the polymerization termination reaction. The above functional groups can also be generated by, for example, hydrolysis of a polyester.

For example, the functional group equivalent weight (weight-average molecular weight per the functional group) of the polyester can be appropriately determined in consideration of, for example, the number of functional groups and the functional group equivalent weight of the chain extender.

Examples of the polyesters having a naphthalene structure that are commercially available include TQB-KET30 (trade name, manufactured by Teijin Chemicals Ltd.) and PELPRENE EN type (trade name, manufactured by Toyobo Co., Ltd.).

The polyesters having a naphthalene structure may be used alone or in combination of two or more thereof.

The content of the chain-extended product of a polyester having a naphthalene structure in the cover layer when the cover layer is formed of a single layer and the content of the chain-extended product of a polyester having a naphthalene structure in the outermost layer when the cover layer is formed of a plurality of layers are preferably 50% by mass or more, more preferably 60% by mass or more, still more preferably 70% by mass or more, even more preferably 80% by mass or more, and yet still more preferably 90% by mass or more. When the cover layer is formed of a single layer, the cover layer may be a layer composed of a chain-extended product of a polyester having a naphthalene structure. When the cover layer is formed of a plurality of layers, the outermost layer may be a layer composed of a chain-extended product of a polyester having a naphthalene structure.

The cover layer in the case of the cover layer formed of a single layer and the outermost layer in the case of the cover layer formed of a plurality of layers can be composed of a blend of a chain-extended product of a polyester having a naphthalene structure and at least one of a polymer other than a polyester having a naphthalene structure or a chain-extended product thereof. In this case, polymers generally used as a covering material that forms a flexible tube for an endoscope can be widely applied to the polymer other than a polyester having a naphthalene structure. Examples of such a polymer include polyesters having no naphthalene structures, polyurethanes, and polyamides.

When the cover layer is formed of a plurality of layers, a layer other than the outermost layer also preferably includes at least one of a polyester having a naphthalene structure or a chain-extended product thereof.

Each of the polymers and chain-extended products thereof that can be used as the cover layer in the present invention preferably has a molecular weight of 10,000 to 1,000,000, more preferably has a molecular weight of 20,000 to 500,000, and still more preferably has a molecular weight of 50,000 to 300,000.

In the present invention, the molecular weight of the polymer constituting the cover layer means a weight-average molecular weight unless otherwise specified. The weight-average molecular weight can be measured by gel permeation chromatography (GPC) as a molecular weight in terms of polystyrene. Specific measurement conditions are described below.

The weight-average molecular weight can be measured by gel permeation chromatography using an HLC-8220 GPC apparatus (trade name, manufactured by Tosoh Corporation) with chloroform as an eluant and G3000HXL+G2000HXL (each of which is a trade name, manufactured by Tosoh Corporation) as columns at 23° C. and a flow rate of 1 mL/min, while detection is performed with a refractive index (RI) detector.

In the specification of this application, the number-average molecular weight can be measured under the same conditions as those for the weight-average molecular weight. In the specification of this application, when a numerical range of the weight-average molecular weight of a compound is described, the numerical range is also preferred as a numerical range of the number-average molecular weight of the compound.

Chain Extender

The chain-extended product of a polyester having a naphthalene structure used in the present invention is prepared by using at least one chain extender selected from the group consisting of (A) an epoxy compound, (B) an isocyanate compound, (C) an amine compound, (D) an oxazoline compound, (E) a carbodiimide compound having a molecular weight of less than 3,000, and (F) a carboxylic anhydride.

(A) Epoxy Compound

The epoxy compound used as the chain extender in the present invention is not particularly limited, and, for example, epoxy compounds disclosed in JP2008-115293A can be used.

The epoxy compound may be either a monofunctional epoxy compound or a polyfunctional epoxy compound and is preferably a polyfunctional epoxy compound. The number of functional groups (the number of epoxy groups per molecule) of the polyfunctional epoxy compound is preferably 2 to 6, more preferably 2 to 5, and still more preferably 2 to 4 in view of sterilization durability, bending durability, and surface smoothness of the flexible tube for an endoscope.

The epoxy compound preferably has a molecular weight of 100 to 1,000, and more preferably 200 to 600. When the epoxy compound has a molecular weight distribution, the weight-average molecular weight (Mw) of the epoxy compound is preferably 200 to 1,000, and more preferably 300 to 800. In the present invention, the weight-average molecular weight of the chain extender can be measured by GPC as a weight-average molecular weight in terms of polystyrene. Specific measurement conditions are described below.

The weight-average molecular weight can be measured by gel permeation chromatography using an HLC-8220 GPC apparatus (trade name, manufactured by Tosoh Corporation) with tetrahydrofuran as an eluant and G3000HXL+G2000HXL (each of which is a trade name, manufactured by Tosoh Corporation) as columns at 23° C. and a flow rate of 1 mL/min, while detection is performed with a refractive index (RI) detector.

The functional group equivalent weight (molecular weight or weight-average molecular weight per epoxy group) of the epoxy compound is not particularly limited, but is preferably 50 to 300, and more preferably 70 to 200.

Specific examples of the epoxy compound include a diglycidyl ether of a dihydric phenol (diglycidyl ether including a structure derived from a compound having two hydroxy groups bonded to a benzene ring or naphthalene ring), a polyglycidyl ether of a polyhydric (trihydric or higher) phenol (diglycidyl ether including a structure derived from a compound having three or more hydroxy groups bonded to a benzene ring or naphthalene ring), a diglycidyl ether of an aliphatic dihydric alcohol or a polymeric diol, a polyglycidyl ether of a trihydric or higher aliphatic alcohol, an epoxy-modified silicone, a glycidyl ester, a glycidyl amine, a linear aliphatic epoxide, an alicyclic epoxide, and a urethane-modified epoxy compound having a urethane bond in the structure.

The diglycidyl ether of a dihydric phenol is not particularly limited but is preferably a diglycidyl ether of a dihydric phenol (having 6 to 30 carbon atoms). Examples thereof include bisphenol F diglycidyl ether, bisphenol A diglycidyl ether, bisphenol B diglycidyl ether, bisphenol AD diglycidyl ether, bisphenol S diglycidyl ether, halogenated bisphenol A diglycidyl ethers (such as tetrachlorobisphenol A diglycidyl ether), catechin diglycidyl ether, resorcinol diglycidyl ether, hydroquinone diglycidyl ether, 1,6-dihydroxynaphthalene diglycidyl ether, dihydroxybiphenyl diglycidyl ether, octachloro-4,4'-dihydroxybiphenyl diglycidyl ether, tetramethylbiphenyl diglycidyl ether, 9,9'-bis(4-hydroxyphenyl) fluorene diglycidyl ether, and a diglycidyl ether obtained from a reaction between two moles of bisphenol A and three moles of epichlorohydrin.

The polyglycidyl ether of a polyhydric (trihydric or higher) phenol is not particularly limited but is preferably one having 6 or more carbon atoms and a Mw of 5,000 or less. Examples thereof include pyrogallol triglycidyl ether, dihydroxynaphthylcresol triglycidyl ether, tris(hydroxyphenyl)methane triglycidyl ether, dinaphthyltriol triglycidyl ether, 4,4'-oxybis(1,4-phenylethyl)phenyl glycidyl ether, bis(dihydroxynaphthalene)tetraglycidyl ether, glycidyl ethers of phenol or cresol-novolac resins (Mw: 200 to 5,000), glycidyl ethers of limonene-phenol-novolac resins (Mw: 400 to 5,000), polyglycidyl ethers of polyphenols (Mw: 400 to 5,000) obtained by condensation reaction between phenol and glyoxal, glutaraldehyde, or formaldehyde, and polyglycidyl ethers of polyphenols having a Mw of 400 to 5,000 and obtained by condensation reaction between resorcin and acetone.

The diglycidyl ether of an aliphatic dihydric alcohol or a polymeric diol is not particularly limited but is preferably a diglycidyl ether of an aliphatic dihydric alcohol having 2 to 100 carbon atoms or a polymeric diol having a Mw of 150 to 5,000. Examples thereof include ethylene glycol diglycidyl ether, propylene glycol diglycidyl ether, tetramethylene glycol diglycidyl ether, 1,6-hexanediol diglycidyl ether, polyethylene glycol (Mw: 150 to 4,000)diglycidyl ether, polypropylene glycol (Mw: 180 to 5,000)diglycidyl ether, polytetramethylene glycol (Mw: 200 to 5,000)diglycidyl ether, and neopentyl glycol diglycidyl ether.

The polyglycidyl ether of a trihydric or higher aliphatic alcohol is not particularly limited but is preferably a glycidyl ether having 3 or more carbon atoms and a Mw of 10,000 or less. Examples thereof include trimethylolpropane triglycidyl ether, glycerol triglycidyl ether, pentaerythritol tetraglycidyl ether, sorbitol hexaglyceryl ether, and poly(n (the number of repetitions of "—$CH_2$—CH(OH)—$CH_2$—O—")=2 to 5)glycerol polyglycidyl ethers.

The epoxy-modified silicone is not particularly limited but is preferably a glycidyl ether of a polydialkylsiloxane (for example, polydimethylsiloxane) having two or more hydroxyl groups and a Mw of 200 to 2,000. Examples thereof include 1,3-bis(3-glycidoxypropyl)-1,1,3,3-tetramethyldisiloxane and 1,3-bis(3-glycidoxypropyl)-1,1,3,3-poly(n (the number of repetitions of "—Si—O—")=2 to 20)tetramethyldisiloxane.

The glycidyl ester is not particularly limited but is preferably a glycidyl ester of a divalent or higher aromatic carboxylic acid, aliphatic carboxylic acid, or alicyclic carboxylic acid having 6 or more carbon atoms. Examples thereof include glycidyl esters of aromatic carboxylic acids, such as glycidyl esters of phthalic acids (such as phthalic acid diglycidyl ester, isophthalic acid diglycidyl ester, and terephthalic acid diglycidyl ether) and trimellitic acid triglycidyl ester; aromatic nucleus hydrogenated products of the glycidyl esters of aromatic carboxylic acids; and glycidyl esters of aliphatic or alicyclic carboxylic acids such as dimer acid diglycidyl ester, diglycidyl oxalate, diglycidyl malate, diglycidyl succinate, diglycidyl glutarate, diglycidyl adipate, and (co)polymers of glycidyl (meth)acrylate (with a degree of polymerization of, for example, 2 to 10).

The glycidyl amine is not particularly limited but is preferably a glycidyl amine of an aromatic amine having 6 or more carbon atoms and 2 or more active hydrogen atoms, or a glycidyl amine of an alicyclic or heterocyclic amine having 5 or more carbon atoms and 2 or more active hydrogen atoms. Examples thereof include glycidyl amines of aromatic amines such as N,N-diglycidylaniline, N,N-diglycidyl toluidine, N,N,N',N'-tetraglycidyl diaminodiphenylmethane, N,N,N',N'-tetraglycidyl diaminodiphenylsulfone, N,N,N',N'-tetraglycidyl diaminodiphenylmethane (tetraglycidyl diaminodiphenylmethane), and N,N,O-triglycidyl aminophenol; N,N,N',N'-tetraglycidyl xylylenediamine, glycidyl amines of aliphatic amines such as N,N,N',N'-tetraglycidyl hexamethylenediamine; a hydrogenated compound of N,N,N',N'-tetraglycidyl xylylenediamine, glycidyl amines of alicyclic amines such as N,N,N',N'-tetraglycidyl cyclohexanediamine; and glycidyl amines of heterocyclic amines such as trisglycidyl melamine.

The linear aliphatic epoxide is not particularly limited but is preferably a divalent or higher linear aliphatic epoxide having 6 or more carbon atoms. Examples thereof include epoxidized (poly)alkadienes (for example, epoxidized butadiene (Mw: 260 to 2,500) having an epoxy equivalent of 130 to 1,000), and epoxidized fats and oils (epoxidized soybean oils (Mw: 130 to 2,500)).

The alicyclic epoxide is not particularly limited but is preferably an alicyclic epoxide having 6 or more carbon atoms, a Mw of 2,500 or less, and two or more epoxy groups. Examples thereof include vinylcyclohexene dioxide, limonene dioxide, dicyclopentadiene dioxide, bis(2,3-epoxycyclopentyl) ether, ethylene glycol bisepoxydicyclopentyl ether, bis(3,4-epoxy-6-methylcyclohexylmethyl) adipate, and bis(3,4-epoxy-6-methylcyclohexylmethyl)butylamine. Also included are nuclear hydrogenated products of the above epoxy compounds of phenols.

The urethane-modified epoxy compound having a urethane bond in the structure is not particularly limited. Examples thereof include reaction products of a polyether urethane oligomer (Mw: 200 to 2,500, for example, an isocyanate group-terminated urethane prepolymer obtained by reacting a polyether diol with a diisocyanate) and glycidol.

(B) Isocyanate Compound

The isocyanate compound used as the chain extender in the present invention is not particularly limited, and, for example, isocyanate compounds disclosed in WO2014/157375A can be used.

The isocyanate compound may be either a monofunctional isocyanate compound or a polyfunctional isocyanate compound and is preferably a polyfunctional isocyanate compound. The number of functional groups (the number of isocyanato groups per molecule) of the polyfunctional isocyanate compound is preferably 2 or 3, and more preferably 3 in view of sterilization durability, bending durability, and surface smoothness of the flexible tube for an endoscope.

The molecular weight of the isocyanate compound is preferably 100 or more, and more preferably 150 or more. When the isocyanate compound has a molecular weight distribution, the weight-average molecular weight of the isocyanate compound is preferably 150 to 10,000, more preferably 200 to 10,000, and still more preferably 300 to 5,000.

Specific examples of the monofunctional isocyanate compound include butyl isocyanate, isopropyl isocyanate, 2-chloroethyl isocyanate, phenyl isocyanate, p-bromophenyl isocyanate, m-chlorophenyl isocyanate, o-chlorophenyl isocyanate, p-chlorophenyl isocyanate, 2,5-dichlorophenyl isocyanate, 3,4-dichlorophenyl isocyanate, 2,6-dimethylphenyl isocyanate, o-fluorophenyl isocyanate, p-fluorophenyl isocyanate, m-tolyl isocyanate, p-tolyl isocyanate, o-trifluoromethylphenyl isocyanate, m-trifluoromethylphenyl isocyanate, and benzyl isocyanate.

Specific examples of the polyfunctional isocyanate compound include hexamethylene diisocyanate, 2,4-toluylene diisocyanate, 2,6-toluylene diisocyanate, 1,5-naphthalene diisocyanate, diphenylmethane-4,4'-diisocyanate, 2,2-dimethyldiphenylmethane-4,4'-diisocyanate, tolidine diisocyanate, isophorone diisocyanate, xylylene diisocyanate, 1,3-bis(isocyanatomethyl)cyclohexane, 1,3-bis(isocyanatomethyl)benzene, p-phenylene diisocyanate, 1,3,6-hexamethylene triisocyanate, bicycloheptane triisocyanate, tris-(3-isocyanato-4-methylphenyl)isocyanurate, and tris-(6-isocyanatohexyl)isocyanurate (another name: 1,3,5-tris(6-isocyanatohex-1-yl)-1,3,5-triazine-2,4,6 (1H, 3H,5H)-trione).

Furthermore, for example, a terminal isocyanate group-containing compound obtained by a reaction between the above polyfunctional isocyanate compound and an active hydrogen compound can also be used. Examples of such a compound include a terminal isocyanate group-containing addition reaction product obtained by a reaction between toluylene diisocyanate and trimethylolpropane, and a terminal isocyanate group-containing addition reaction product obtained by a reaction between toluylene diisocyanate and pentaerythritol.

(C) Amine Compound

The amine compound used as the chain extender in the present invention is not particularly limited, and, for example, amine compounds disclosed in JP2008-545606A and JP2018-182199A can be used.

The amino group of the amine compound may be either an unsubstituted amino group or a monosubstituted amino group, and is preferably an unsubstituted amino group. Hereinafter, an amine compound having an unsubstituted amino group is referred to as a "primary amine compound", and a compound having a monosubstituted amino group is referred to as a "secondary amine compound". However, an amine compound having an unsubstituted amino group and a monosubstituted amino group is classified into the primary amine compound.

The number of functional groups (the number of amino groups per molecule) of the amine compound is preferably 2 to 4, more preferably 3 or 4, and still more preferably 4 in view of sterilization durability, bending durability, and surface smoothness of the flexible tube for an endoscope.

The molecular weight of the amine compound is preferably 50 or more, and more preferably 150 or more. When the amine compound has a molecular weight distribution, the weight-average molecular weight of the amine compound is preferably 200 to 10,000, and more preferably 300 to 8,000.

The amine compound is preferably an amine compound having a ring structure, preferably an alicyclic amine compound (an amine compound having an alicyclic ring) and an aromatic amine compound (an amine compound having at least one of an aromatic hydrocarbon ring or an aromatic heterocycle), and more preferably an aromatic amine compound. Note that an amine compound having an alicyclic ring and an aromatic ring (an aromatic hydrocarbon ring and an aromatic heterocycle) is classified into the aromatic amine compound.

The amine compound may have a plurality of ring structures in the molecule, and the plurality of ring structures may be the same or different.

A specific example of the alicyclic primary amine compound (amine compound having an alicyclic ring and an unsubstituted amino group) is cyclohexylamine.

A specific example of the alicyclic secondary amine compound (amine compound having an alicyclic ring and a monosubstituted amino group) is N-methylcyclohexylamine.

Specific examples of the aromatic primary amine compound (amine compound having an aromatic ring and an unsubstituted amino group) include diaminodiphenyl ether, xylenediamine (preferably, para-xylenediamine), diaminobenzene, diaminotoluene, methylenedianiline, dimethyldiaminobiphenyl, bis(trifluoromethyl)diaminobiphenyl, diaminobenzophenone, diaminobenzanilide, bis(aminophenyl) fluorene, bis(aminophenoxy)benzene, bis(aminophenoxy)biphenyl, dicarboxydiaminodiphenylmethane, diaminoresorcin, dihydroxybenzidine, diaminobenzidine, 4,4'-diaminodiphenylmethane, 1,3,5-triaminophenoxybenzene, 2,2'-dimethylbenzidine, tris(4-aminophenyl)amine, 2,7-diaminofluorene, tetrakis(4-aminophenyl)methane, 2,4'-diaminodiphenylmethane, (o-tolyl)biguanide, melamine(1,3,5-triazine-2,4,6-triamine), ammeline, melam, melem, 5-thiazolamine, 2-aminobenzothiazole, N,N',N"-tris(4-aminophenyl)-1,3,5-triazine-2,4,6-triamine, and 2,4-diamino-6-phenyl-1,3,5-triazine.

Specific examples of the aromatic secondary amine compound (amine compound having an aromatic ring and a monosubstituted amino group) include 1,9-diaminofluorene, dibenzylamine, N,N'-di-isopropyl-p-phenylenediamine, N,N'-di-s-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)diphenylamine, diphenylamine (which may have an alkyl group having 1 to 8 carbon atoms), 4-isopropoxydiphenylamine, N-phenyl-1-naphthylamine (which may have a t-octyl group), N-(4-t-octylphenyl)-1-naphthylamine, N-phenyl-2-naphthylamine, octylated diphenylamines (e.g., p,p'-di-t-octyldiphenylamine), 4-n-butylaminophenol, 4-butyrylaminophenol, 4-nonanoylaminophenol, 4-dodecanoylaminophenol, 4-octadecanoylaminophenol, bis(4-methoxyphenyl)amine, 1,2-bis[(2-methylphenyl)-amino]ethane, 1,2-bis(phenylamino)propane, bis[4-(1',3'-dimethylbutyl) phenyl]amine, 2,3-dihydro-3,3-dimethyl-4H-1,4-benzothiazine, and phenothiazine (which may have an alkyl group having 1 to 8 carbon atoms).

In the present invention, an aromatic primary amine compound is preferably used as the (C) amine compound in view of sterilization durability, bending durability, and surface smoothness of the flexible tube for an endoscope.

(D) Oxazoline Compound

The oxazoline compound used as the chain extender in the present invention is not particularly limited, and, for example, oxazoline compounds disclosed in JP2020-56006A and JP2016-4978A can be used.

The oxazoline compound may be either a monofunctional oxazoline compound or a polyfunctional oxazoline compound and is preferably a polyfunctional oxazoline compound. The number of functional groups (the number of oxazoline groups per molecule) of the polyfunctional oxazoline compound is preferably 2 to 100, more preferably 2 to 50, and still more preferably 2 to 20.

The molecular weight of the oxazoline compound is preferably 100 or more, and more preferably 200 or more. When the oxazoline compound has a molecular weight distribution, that is, when the oxazoline compound is a polymeric oxazoline compound, the weight-average molecular weight of the oxazoline compound is preferably 200 to 500,000, more preferably 500 to 500,000, more preferably 5,000 to 500,000, and still more preferably 10,000 to 200,000.

Examples of the oxazoline compound include bisoxazoline compounds and polymeric oxazoline compounds (that is, polymers having an oxazoline group, for example, an oxazoline group-containing polystyrene, an oxazoline group-containing acrylic polymer, and an oxazoline group-containing styrene-(meth)acrylic copolymer). In view of sterilization durability, bending durability, and surface smoothness of the flexible tube for an endoscope, a polymeric oxazoline compound is preferable.

The oxazoline content of the polymeric oxazoline compound is not particularly limited, but is preferably 0.05 to 1.5 mmol/g, and more preferably 0.1 to 1.0 mmol/g.

Examples of bisoxazoline compounds include 2,2'-bis(2-oxazoline), 2,2'-bis(4-methyl-2-oxazoline), 2,2'-bis(4,4-dimethyl-2-oxazoline), 2,2'-bis(4-ethyl-2-oxazoline), 2,2'-bis (4,4'-diethyl-2-oxazoline), 2,2'-bis(4-propyl-2-oxazoline), 2,2'-bis(4-butyl-2-oxazoline), 2,2'-bis(4-hexyl-2-oxazoline), 2,2'-bis(4-phenyl-2-oxazoline), 2,2'-bis(4-cyclohexyl-2-oxazoline), 2,2'-bis(4-benzyl-2-oxazoline), 2,2'-p-phenylenebis(2-oxazoline), 2,2'-m-phenylenebis(2-oxazoline) (another name: 2,2'-(1,3-phenylene)bis(2-oxazoline)), 2,2'-o-phenylenebis(2-oxazoline), 2,2'-p-phenylenebis(4-methyl-2-oxazoline), 2,2'-p-phenylenebis(4,4-dimethyl-2-oxazoline), 2,2'-m-phenylenebis(4-methyl-2-oxazoline), 2,2'-m-phenylenebis(4,4-dimethyl-2-oxazoline), 2,2'-ethylenebis(2-oxazoline), 2,2'-tetramethylenebis(2-oxazoline), 2,2'-hexamethylenebis(2-oxazoline), 2,2'-octamethylenebis (2-oxazoline), 2,2'-decamethylenebis(2-oxazoline), 2,2'-ethylenebis(4-methyl-2-oxazoline), 2,2'-tetramethylenebis(4,4-dimethyl-2-oxazoline), 2,2'-9,9'-diphenoxyethanebis(2-oxazoline), 2,2'-cyclohexylenebis(2-oxazoline), and 2,2'-diphenylenebis(2-oxazoline).

Specific examples of polymeric oxazoline compounds include EPOCROS series manufactured by Nippon Shokubai Co., Ltd. (for example, EPOCROS K2010E, EPOCROS K2020E, EPOCROS K2030E, EPOCROS WS500, EPOCROS WS700, and EPOCROS RPS-1005, all of which are trade names).

(E) Carbodiimide Compound Having Molecular Weight of Less Than 3,000

The carbodiimide compound having a molecular weight of less than 3,000 (hereinafter, also simply referred to as a "carbodiimide compound") used as the chain extender in the present invention is not particularly limited, and, for example, carbodiimide compounds having a molecular weight of less than 3,000 and disclosed in JP2019-9263A and JP2016-182685A can be used.

When the carbodiimide compound has a molecular weight distribution, the "molecular weight" means a weight-average molecular weight.

The molecular weight of the carbodiimide compound is preferably 150 or more, and more preferably 200 or more. When the carbodiimide compound has a molecular weight distribution, the weight-average molecular weight of the carbodiimide compound is preferably 200 to 3,000, and more preferably 500 to 2,000.

The carbodiimide compound may be either a monofunctional carbodiimide compound or a polyfunctional carbodiimide compound. The number of functional groups (the number of carbodiimide groups per molecule) of the carbodiimide compound is preferably 1 to 6, more preferably 1 to 3, and still more preferably 1.

The structure of the carbodiimide compound is not particularly limited and may be either linear or cyclic. A carbodiimide compound having a ring structure is preferable in view of sterilization durability, bending durability, and surface smoothness of the flexible tube for an endoscope.

The "carbodiimide compound having a ring structure" means a compound having a ring including a carbodiimide group as a ring-forming component, that is, a compound having a ring (carbodiimide ring) in which nitrogen atoms and a carbon atom that form the carbodiimide group are ring-forming atoms.

The number of carbodiimide groups forming the carbodiimide ring may be one or two or more, but is preferably one.

The carbodiimide ring is preferably a 4- to 16-membered ring, and more preferably a 6- to 12-membered ring. Examples of the carbodiimide ring-forming atoms other than the carbodiimide group include a carbon atom, an oxygen atom, a nitrogen atom, and a sulfur atom.

Specific examples of the monofunctional carbodiimide compound include dicyclohexylcarbodiimide, diisopropylcarbodiimide, dimethylcarbodiimide, diisobutylcarbodiimide, dioctylcarbodiimide, t-butylisopropylcarbodiimide, diphenylcarbodiimide, di-t-butylcarbodiimide, di-β-naphthylcarbodiimide, N,N'-di-2,6-diisopropylphenylcarbodiimide, and compounds having a carbodiimide ring (the number of carbodiimide groups forming the ring is 1).

Specific examples of the polyfunctional carbodiimide compound include a polycarbodiimide compound, that is, a polymer having a carbodiimide group in a repeating unit. The degree of polymerization of the polymer is 2 or more, and preferably 4 or more. On the other hand, the degree of polymerization is preferably 40 or less, and more preferably 30 or less.

Specific examples of the polyfunctional carbodiimide compound include a compound having two or more carbodiimide rings (the number of carbodiimide groups forming the ring is 1) and a compound having one carbodiimide ring (the number of carbodiimide groups forming the ring is 2 or more).

Specific examples of industrially available carbodiimide compounds include Carbodilite HMV-8CA (manufactured by Nisshinbo Chemical Inc.), Carbodilite LA-1 (manufactured by Nisshinbo Chemical Inc.), Stabaxol I (manufactured by Rhein Chemie GmbH), Stabaxol P (manufactured by Rhein Chemie GmbH), Stabaxol P100 (manufactured by Rhein Chemie GmbH), Stabaxol P400 (manufactured by Rhein Chemie GmbH), STABILIZER 9000 (manufactured by Raschig Chemie GmbH), and CARBOSISTA TCC-NP (manufactured by Teijin Limited) (all of which are trade names).

The carbodiimide compound having a ring structure can be prepared by the method described in, for example, WO2011/093478A. The polycarbodiimide compound can be prepared by the methods described in, for example, U.S. Pat. No. 2,941,956A, JP1972-33279B (JP-S47-33279B), J. Org. Chem. Vol. 28, pp. 2069 to 2075 (1963), and Chemical Review 1981, Vol. 81, No. 4, pp. 619 to 621.

Examples of an organic diisocyanate which is a starting material for producing the polycarbodiimide compound include aromatic diisocyanates, aliphatic diisocyanates, alicyclic diisocyanates, and mixtures thereof. Specific examples thereof include 1,5-naphthalene diisocyanate, 4,4'-diphenylmethane diisocyanate, 4,4'-diphenyldimethylmethane diisocyanate, 1,3-phenylene diisocyanate, 1,4-phenylene diisocyanate, 2,4-tolylene diisocyanate, 2,6-tolylene diisocyanate, mixtures of 2,4-tolylene diisocyanate and 2,6-tolylene diisocyanate, hexamethylene diisocyanate, cyclohexane-1,4-diisocyanate, xylylene diisocyanate, isophorone diisocyanate, 4,4'-dicyclohexylmethane diisocyanate, methylcyclohexane diisocyanate, tetramethylxylylene diisocyanate, 2,6-diisopropylphenyl isocyanate, and 1,3,5-triisopropylbenzene-2,4-diisocyanate.

(F) Acid Anhydride

The carboxylic anhydride (anhydride derived from a carboxylic acid) used as the chain extender in the present invention is not particularly limited, and may be either a linear carboxylic anhydride or a cyclic carboxylic anhydride, and is preferably a cyclic carboxylic anhydride.

The number of carboxylic anhydride groups is not particularly limited, but is preferably 1 to 3, and more preferably 2. That is, carboxylic anhydrides (dicarboxylic anhydrides), tetracarboxylic dianhydrides, and hexacarboxylic trianhydrides are preferable, and tetracarboxylic dianhydrides are more preferable in view of sterilization durability, bending durability, and surface smoothness of the flexible tubes for an endoscope.

The molecular weight of the carboxylic anhydride is not particularly limited, but is preferably 150 to 600, and more preferably 180 to 400.

As the carboxylic anhydride (anhydride derived from a carboxylic acid), for example, carboxylic anhydrides disclosed in JP2016-37538A can be used.

Specific examples of the carboxylic anhydrides (dicarboxylic anhydrides) include 4-ethynylphthalic anhydride (abbreviation: 4-EPA), 4-phenylethynylphthalic anhydride, maleic anhydride, citraconic anhydride, itaconic anhydride, allylnadic anhydride, 5-norbornene-2,3-dicarboxylic anhydride, cyclohexene-1,2-dicarboxylic anhydride, exo-3,6-epoxy-1,2,3,6-tetrahydrophthalic anhydride, and allylsuccinic anhydride.

Specific examples of the tetracarboxylic dianhydrides include 3,3',4,4'-biphenyltetracarboxylic dianhydride (abbreviation: s-BPDA), pyromellitic dianhydride (abbreviation: PMDA), 3,3',4,4'-benzophenonetetracarboxylic dianhydride, 2,2',3,3'-benzophenonetetracarboxylic dianhydride, 2,3,3',4'-benzophenonetetracarboxylic dianhydride, 3,3',4,4'-diphenylsulfonetetracarboxylic dianhydride, 2,2',3,3'-diphenylsulfonetetracarboxylic dianhydride, 2,3,3',4'-diphenylsulfonetetracarboxylic dianhydride, 3,3',4,4'-diphenyl ether tetracarboxylic dianhydride (abbreviation: ODPA), 2,2',3,3'-diphenyl ether tetracarboxylic dianhydride, 2,3,3',4'-diphenyl ether tetracarboxylic dianhydride, 2,2-[bis(3,4-dicarboxyphenyl)]hexafluoropropane dianhydride, ethylene glycol bis(anhydro trimellitate), 4,4'-[(isopropylidene)bis(p-phenyleneoxy)]diphthalic dianhydride, cyclobutanetetracarboxylic dianhydride, methylcyclobutane tetracarboxylic dianhydride, cyclopentanetetracarboxylic dianhydride, 1,2,4,5-cyclohexanetetracarboxylic dianhydride, ethanetetracarboxylic dianhydride, butanetetracarboxylic dianhydride, and 3,3',4,4'-bicyclohexyl tetracarboxylic dianhydride.

A specific example of the hexacarboxylic trianhydrides is benzenehexacarboxylic 1,2:3,4:5,6-trianhydride.

In view of sterilization durability, bending durability and surface smoothness of the flexible tube for an endoscope, as the chain extender, at least one of the (B) isocyanate compound, the (C) amine compound, the (D) oxazoline compound, the (E) carbodiimide compound having a molecular weight of less than 3,000, or the (F) carboxylic anhydride is preferably used, and at least one of the (D) oxazoline compound, the (E) carbodiimide compound having a molecular weight of less than 3,000, or the (F) carboxylic anhydride is more preferably used.

In these combinations of the chain extenders, preferred forms of each chain extender are as described above. Specifically, among these combinations, a combination in which each chain extender is in a preferred form is more preferred.

In the present invention, the chain extenders may be used alone or in combination of two or more thereof.

The chain-extended product of a polyester having a naphthalene structure can be prepared by applying general reaction conditions for a polymer and a chain extender. For example, the preparation can be performed with reference to JP2014-188217A. Specifically, for example, the preparation can be performed by melt-kneading a mixture containing a polyester having a naphthalene structure and a chain extender to cause the polyester and the chain extender to react with each other. The melt-kneading can be performed, for example, at a heating temperature of 150° C. to 300° C. using a kneading machine (such as a twin-screw kneader). A catalyst may be used in the preparation of the chain-extended product of a polyester having a naphthalene structure, as needed.

The amount of the chain extender used in the preparation of the chain-extended product of a polyester having a naphthalene structure is not particularly limited, but is preferably 0.05 parts by mass or more and 3.0 parts by mass or less, more preferably 0.1 parts by mass or more and 2.0 parts by mass or less, and still more preferably 0.2 parts by mass or more and 1.5 parts by mass or less based on 100 parts by mass of the total blending amount of the polyester having a naphthalene structure and the chain extender.

The cover layer may appropriately contain various common additives as long as the effects of the present invention are not impaired. Examples of the additives include a heat-resistant stabilizer, a mineral filler, an impact resistance-improving agent, a plasticizer, a lubricant, a metal soap, a light-resistant auxiliary agent, and a colorant. The contents of the additives in the cover layer can also be appropriately adjusted. Such additives may be derived from the material of the chain-extended product of a polyester having a naphthalene structure to be used or can be added separately from the chain-extended product of a polyester having a naphthalene structure.

Interlayer

In order to improve adhesiveness between the flexible-tube base and the cover layer, an interlayer such as an adhesive layer or a primer layer may be disposed between the flexible-tube base and the cover layer. An example of the adhesive layer is one formed of a composition containing a polymer such as polyurethane and a polyisocyanate compound. An example of the primer layer is one formed of a silane coupling agent. The thickness of the interlayer is not particularly limited and can be, for example, 0.1 to 1.0 mm.

Topcoat Layer

In the flexible tube according to the present invention, a topcoat layer (not illustrated) is disposed on an outer periphery of a cover layer 15 as needed. The material of the top coat layer is not particularly limited, but a urethane coating, an acrylic coating, a fluorine coating, a silicone coating, an epoxy coating, a polyester coating, or the like is applied.

Main purposes of use of the topcoat layer are to protect the surface of the flexible tube or make the surface glossy, to impart slidability, and to impart chemical resistance. Therefore, the topcoat layer preferably has a high modulus of elasticity, a smooth surface, and good chemical resistance.

Method for Producing Flexible Tube

The production of the flexible tube for an endoscope according to the present invention includes a step of forming a cover layer. The step of forming a cover layer includes forming, on an outer periphery of the flexible-tube base, a cover layer using a cover layer-forming material that includes a component derived from a polyester having a naphthalene structure and at least one chain extender selected from the group consisting of (A) an epoxy compound, (B) an isocyanate compound, (C) an amine compound, (D) an oxazoline compound, (E) a carbodiimide compound having a molecular weight of less than 3,000, and (F) a carboxylic anhydride. The formation itself of the cover layer using the cover layer-forming material can be performed by an ordinary method. For example, the cover layer can be formed by subjecting the cover layer-forming material to extrusion coating (forming temperature: 150° C. to 250° C.). The cover layer-forming material can be prepared by, for example, kneading the components used for the cover layer-forming material with a twin-screw kneader.

Endoscopic Medical Device

The flexible tube according to the present invention is widely applicable to endoscopic medical devices. For example, the flexible tube according to the present invention is applicable to an endoscope equipped with a clip or wire at the distal end thereof or to a device equipped with a basket or brush. Note that the term "endoscopic medical device" is meant to broadly include, besides medical devices that include an endoscope as a basic structure, medical devices and diagnosis and treatment devices that include an insertion section having flexibility and that are introduced and used in the inside of the body, such as remote-controlled medical devices.

An endoscopic medical device according to the present invention has an insertion section in which the flexible tube for an endoscope according to the present invention is incorporated. That is, a method for producing an endoscopic medical device according to the present invention includes incorporating, into an insertion section of an endoscopic medical device, a flexible tube for an endoscope according to the present invention or a flexible tube for an endoscope, the flexible tube being obtained by the method for producing a flexible tube for an endoscope according to the present invention.

An electronic endoscope will now be described as an example of an endoscopic medical device according to a preferred embodiment of the present invention. An electronic endoscope includes a flexible tube for an endoscope, the flexible tube being incorporated therein, and is used as a medical device for, for example, examining the inside of the body cavity by inserting the flexible tube into the inside of the body cavity. In an example illustrated in FIG. 1, an electronic endoscope 2 includes an insertion section 3 to be inserted into the body cavity, a main-body operation section 5 connected to a proximal end portion of the insertion section 3, and a universal cord 6 to be connected to a processor device or a light source device. The insertion section 3 is constituted by a flexible tube **3*a* connected to the main-body operation section 5, an angle portion 3*b* connected to the flexible tube 3*a*, and a tip portion 3*c* connected to the distal end of the angle portion 3*b* and including therein an imaging device (not illustrated) for capturing an image of the inside of the body cavity. The flexible tube 3*a*, which accounts for most of the length of the insertion section 3**, has flexibility across substantially the entire length thereof and is configured so that, in particular, a portion to be inserted into the inside of the body cavity or the like has higher flexibility.

Flexible Tube

The constituent material of the flexible-tube base is not particularly limited, and the flexible tube preferably has a flexible-tube base containing metal as the constituent material.

Figure 2:
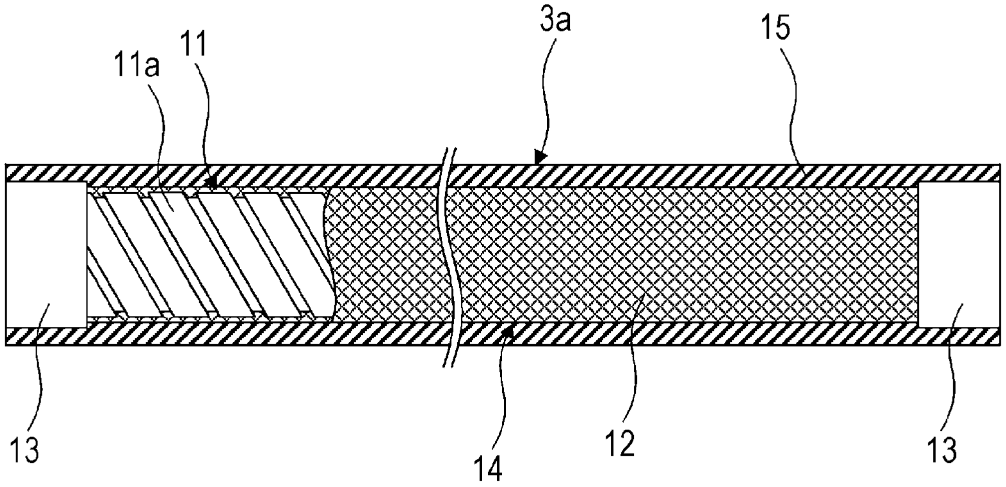
FIG. 2 is a partial sectional view illustrating a schematic configuration of a flexible tube for an endoscope.

As illustrated in FIG. 2, a flexible-tube base 14 preferably has a form in which a spiral tube 11 disposed on the innermost side and formed by spirally winding a metal strip **11*a* is covered with a tubular mesh 12 formed by weaving metal wires, and caps 13 are fitted to both ends of the flexible-tube base 14. The metal constituting the flexible-tube base 14 preferably has a surface that has been subjected to passivation treatment in order to prevent corrosion. That is, the flexible-tube base 14** preferably has a passivation film on an outer periphery thereof. This passivation treatment can be performed by an ordinary method. A passivation film can be formed on a surface of metal by, for example, immersing the metal in a solution including a strong oxidizing agent such as nitric acid, heating the metal in air (oxygen) or water (water vapor), or anodizing the metal in a solution including an oxidizing agent.

The metal that constitutes the flexible-tube base 14 is preferably stainless steel. The surface of stainless steel is usually in a state in which chromium and oxygen are bound together to form a passivation film. However, even when stainless steel is used as the constituent material of the flexible-tube base 14, the stainless steel is preferably subjected to the passivation treatment described above in order to more reliably form a more uniform passivation film over the entire surface of the stainless steel.

In this embodiment, the cover layer 15 is formed with a substantially uniform thickness in the longitudinal direction (axial direction) of the flexible-tube base 14. The cover layer 15 has a thickness of, for example, 0.1 to 0.6 mm, and the flexible tube **3*a* has an outer diameter D of, for example, 1.7 to 13.5 mm, preferably 3.0 to 8.0 mm. Furthermore, the flexible-tube base 14 has an outer diameter of, for example, 1.6 to 12.5 mm, preferably 2.2 to 7.8 mm. When the flexible tube according to the present invention is used for insertion into the bronchus, the thickness of the cover layer 15 is preferably 0.1 to 0.3 mm, the outer diameter D of the flexible tube 3***a* is preferably 3.0 to 5.0 mm, and the outer diameter of the flexible-tube base 14 is preferably 2.4 to 4.8 mm.

EXAMPLES

Hereafter, the present invention will be described in more detail by way of Examples. However, these Examples should not be construed as limiting the present invention.

Preparation of Cover Layer-Forming Material

A mixture prepared by mixing the components shown in Tables 1-1 to 1-5 below (hereinafter, Tables 1-1 to 1-5 are collectively referred to as Table 1) at the blending ratio (parts by mass) shown in Table 1 below was introduced into a twin-screw kneader (manufactured by Technovel Corporation, KZW15-30MG, trade name) in which a barrel temperature and a die temperature were set to 220° C., and kneaded at a screw rotation speed of 100 rpm. A strand in a molten state discharged from the twin-screw kneader was cooled in a water tank and then cut with a pelletizer to obtain a pellet-shaped cover layer-forming material.

Preparation of Flexible-Tube Base

Flexible-tube bases used in Examples and Comparative Examples will be descried with reference to FIG. 2.

Each of the flexible-tube bases prepared had a form in which a spiral tube 11 was formed by using a metal strip 11*a* made of stainless steel, and the spiral tube 11 was covered with a tubular mesh 12 formed by weaving stainless steel fibers. The flexible-tube base has a length of 80 cm and a diameter of 12 mm. The stainless steel flexible-tube base has a passivation layer on a surface thereof, the passivation layer being formed by annealing treatment (heating treatment) at the time of the formation of the spiral tube and the tubular mesh.

Formation of Adhesive Layer

An adhesive layer-forming liquid prepared by mixing 10 parts by mass of a polyester polyurethane ("N-2304" (trade name) manufactured by Nippon Polyurethane Industry Co., Ltd.), 1 part by mass of a polyisocyanate ("CORONATE L" (trade name) manufactured by Nippon Polyurethane Industry Co., Ltd.), and 20 parts by mass of methyl ethyl ketone was uniformly applied to an outer periphery of the stainless steel flexible-tube base, and dried at room temperature for two hours. Subsequently, heat treatment was further performed at 150° C. for two hours to prepare a flexible-tube base having an adhesive layer on the outer periphery (resin-coated surface). The adhesive layer had a thickness of 0.3 mm.

Formation of Cover Layer

The outer periphery of the flexible-tube base having the adhesive layer thereon was covered with the cover layer-forming material prepared above by extrusion (molding temperature: 220° C.) to produce a flexible tube for an endoscope, the flexible tube having a cover layer. The cover layer had a thickness of 0.4 mm.

Test Example 1 Surface Smoothness

The cover layer was peeled off from the above-produced flexible tube for an endoscope, and a test piece with a size of 2 cm×2 cm was cut out and placed on a smooth metal plate. The surface of the test piece was irradiated with light at an incidence angle of 60° with a surface glossmeter (variable-angle glossmeter "VG-2000" (trade name) manufactured by Nippon Denshoku Industries Co., Ltd.), and the reflectance was measured and evaluated on the basis of the following evaluation scale. "C" or higher is satisfactory in this test. The higher the reflectance, the better the surface smoothness of the flexible tube for an endoscope.

Evaluation Scale

A: 90% or more

B: 80% or more and less than 90%

C: 70% or more and less than 80%

D: less than 70%

Test Example 2 Bending Durability

One end of the produced flexible tube (length: 80 cm) for an endoscope is referred to as an end a, and the other end is referred to as an end b. The center of the flexible tube for an endoscope in the length direction was placed on (brought into contact with) the apex of a fixed pulley, and the flexible tube was then bent into a U-shape (radius of curvature: 5 cm) along the circumference of the pulley. In this U-shaped bent state, a half (15.7 cm) of the circumference of the pulley is in contact with the flexible tube. The ends a and b were grasped, and the end a and the end b were alternately pulled as follows.

(1) While the state in which the flexible tube is in contact with the half of the circumference of the pulley is maintained, the end a is pulled such that the terminal of the end a moves 20 cm.

(2) While the state in which the flexible tube is in contact with the half of the circumference of the pulley is maintained, the end b is pulled such that the terminal of the end b moves 40 cm.

(3) While the state in which the flexible tube is in contact with the half of the circumference of the pulley is maintained, the end a is pulled such that the terminal of the end a moves 20 cm, thereby returning to the initial U-shaped state of (1).

The movements of (1) to (3) were defined as one reciprocating movement, and the number of reciprocations when peeling between the flexible-tube base and the cover layer or cracking of the cover layer occurred was evaluated on the basis of the following evaluation scale. "C" or higher is satisfactory in this test.

Evaluation Scale

AA: 50,000 times or more

A: 10,000 times or more and less than 50,000 times

B: 2,000 times or more and less than 10,000 times

C: 100 times or more and less than 2,000 times

D: less than 100 times

Test Example 3 Sterilization Durability

A test piece with a size of 1 cm×10 cm was cut out in the same manner as in Test Example 1. The test piece was placed in a flow path of an ozone water generating device (trade name: "OWM-10L10P" manufactured by EcoDesign, Inc.), and ozone water having an ozone concentration of 5 ppm was caused to flow at a flow rate of 1 L/min for eight hours. Subsequently, washing was performed with distilled water, and the test piece was dried at 23° C. and 50% RH (relative humidity) for 24 hours. The dried test piece was subjected to a tensile test using a TENSILON universal material testing instrument (trade name: RTF-1210, manufactured by A&D Company, Limited) and evaluated on the basis of the following evaluation scale (an elongation of 100% means that the test piece was stretched by a factor of 2). "C" or higher is satisfactory in this test.

Evaluation Scale

A: Breaking did not occur even when the elongation reached 300%.

B: Breaking did not occur even when the elongation reached 200%, but breaking occurred before the elongation reached 300%.

C: Breaking did not occur even when the elongation reached 100%, but breaking occurred before the elongation reached 200%.

D: Breaking occurred before the elongation reached 100%.

TABLE 1-1

| | | Ex. 1 | Ex. 2 | Ex. 3 | Ex. 4 | Ex. 5 | Ex. 6 | Ex. 7 | Ex. 8 | Ex. 9 | Ex. 10 |
|---|---|---|---|---|---|---|---|---|---|---|---|
| Cover layer-forming material (parts by mass) | (T) Polyester having naphthalene structure | (T-1) 99.5 | (T-1) 99.5 | (T-1) 99.5 | (T-1) 99.5 | (T-1) 99.5 | (T-1) 99.5 | (T-1) 99.5 | (T-1) 99.5 | (T-1) 99.5 | (T-1) 99.5 |
| | (S) Other polymer | | | | | | | | | | |
| | (A) Epoxy compound | (A-1) 0.5 | (A-2) 0.5 | (A-3) 0.5 | | | | | | | |
| | (B) Isocyanate compound | | | | (B-1) 0.5 | (B-2) 0.5 | (B-3) 0.5 | | | | |
| | (C) Amine compound | | | | | | | (C-1) 0.5 | (C-2) 0.5 | (C-3) 0.5 | |
| | (D) Oxazoline compound | | | | | | | | | | (D-1) 0.5 |
| | (E) Carbodiimide compound having molecular weight of less than 3,000 | | | | | | | | | | |
| | (F) Carboxylic anhydride | | | | | | | | | | |
| Evaluation results | Test Example 1 (Surface smoothness) | B | B | C | C | C | B | C | B | B | A |
| | Test Example 2 (Bending durability) | C | C | C | C | B | B | C | C | B | A |
| | Test Example 3 (Sterilization durability) | C | C | B | C | B | A | A | A | A | A |

TABLE 1-2

| | | Ex. 11 | Ex. 12 | Ex. 13 | Ex. 14 | Ex. 15 | Ex. 16 | Ex. 17 | Ex. 18 | Ex. 19 | Ex. 20 |
|---|---|---|---|---|---|---|---|---|---|---|---|
| Cover layer-forming material (parts by mass) | (T) Polyester having naphthalene structure | (T-1) 99.5 | (T-1) 99.5 | (T-1) 99.5 | (T-1) 99.5 | (T-1) 99.5 | (T-1) 99.5 | (T-1) 99.0 | (T-1) 99.9 | (T-1) 99.7 | (T-1) 99.0 |
| | (S) Other polymer | | | | | | | | | | |
| | (A) Epoxy compound | | | | | | | (A-2) 0.5 | | | |
| | (B) Isocyanate compound | | | | | | | | | | |
| | (C) Amine compound | | | | | | | (C-2) 0.5 | | | |
| | (D) Oxazoline compound | (D-2) 0.5 | | | | | | | | | |
| | (E) Carbodiimide compound having molecular weight of less than 3,000 | | (E-1) 0.5 | (E-2) 0.5 | | | | | (E-2) 0.1 | (E-2) 0.3 | (E-2) 1.0 |
| | (F) Carboxylic anhydride | | | | (F-1) 0.5 | (F-2) 0.5 | (F-3) 0.5 | | | | |
| Evaluation results | Test Example 1 (Surface smoothness) | A | B | A | A | A | A | B | A | A | B |
| | Test Example 2 (Bending durability) | AA | A | AA | A | A | A | A | B | A | AA |
| | Test Example 3 (Sterilization durability) | A | A | A | B | A | A | A | B | A | A |

TABLE 1-3

| | | Ex. 21 | Ex. 22 | Ex. 23 | Ex. 24 | Ex. 25 |
|---|---|---|---|---|---|---|
| Cover layer-forming material (parts by mass) | (T) Polyester having naphthalene structure | (T-1) 79.5 | (T-1) 79.5 | (T-1) 79.5 | (T-2) 99.5 | (T-2) 99.5 |
| | (S) Other polymer | (S-1) 20.0 | (S-2) 20.0 | (S-3) 20.0 | | |
| | (A) Epoxy compound | | | | | |
| | (B) Isocyanate compound | | | | | |

TABLE 1-3-continued

| | | Ex. 21 | Ex. 22 | Ex. 23 | Ex. 24 | Ex. 25 |
|---|---|---|---|---|---|---|
| | (C) Amine compound | | | | | |
| | (D) Oxazoline compound | | | | (D-2) 0.5 | |
| | (E) Carbodiimide compound having molecular weight of less than 3,000 | (E-2) 0.5 | (E-2) 0.5 | (E-2) 0.5 | | (E-2) 0.5 |
| | (F) Carboxylic anhydride | | | | | |
| Evaluation results | Test Example 1 (Surface smoothness) | A | A | A | A | A |
| | Test Example 2 (Bending durability) | A | A | A | AA | AA |
| | Test Example 3 (Sterilization durability) | A | A | A | A | A |

TABLE 1-4

| | | Com. 1 | Com. 2 | Com. 3 | Com. 4 | Com. 5 | Com. 6 | Com. 7 | Com. 8 | Com. 9 | Com. 10 |
|---|---|---|---|---|---|---|---|---|---|---|---|
| Cover layer-forming material (parts by mass) | (T) Polyester having naphthalene structure | (T-1) 100.0 | (T-1) 99.5 | | | | | | | | |
| | (S) Other polymer | | | (S-1) 99.5 | (S-1) 99.5 | (S-1) 99.5 | (S-1) 99.5 | (S-1) 99.5 | (S-1) 99.5 | (S-2) 99.5 | (S-2) 99.5 |
| | (A) Epoxy compound | | | (A-3) 0.5 | | | | | | (A-3) 0.5 | |
| | (B) Isocyanate compound | | | | (B-3) 0.5 | | | | | | (B-3) 0.5 |
| | (C) Amine compound | | | | | (C-2) 0.5 | | | | | |
| | (D) Oxazoline compound | | | | | | (D-2) 0.5 | | | | |
| | (E) Carbodiimide compound having molecular weight of less than 3,000 | | (e-3) 0.5 | | | | | (E-2) 0.5 | | | |
| | (F) Carboxylic anhydride | | | | | | | | (F-2) 0.5 | | |
| Evaluation results | Test Example 1 (Surface smoothness) | A | D | B | C | C | B | B | B | C | D |
| | Test Example 2 (Bending durability) | D | C | D | D | D | C | C | C | D | C |
| | Test Example 3 (Sterilization durability) | D | D | D | D | D | D | D | D | D | D |

TABLE 1-5

| | | Com. 11 | Com. 12 | Com. 13 | Com. 14 | Com. 15 | Com. 16 | Com. 17 | Com. 18 | Com. 19 | Com. 20 |
|---|---|---|---|---|---|---|---|---|---|---|---|
| Cover layer-forming material (parts by mass) | (T) Polyester having naphthalene structure | | | | | | | | | | |
| | (S) Other polymer | (S-2) 99.5 | (S-2) 99.5 | (S-2) 99.5 | (S-2) 99.5 | (S-3) 99.5 | (S-3) 99.5 | (S-3) 99.5 | (S-3) 99.5 | (S-3) 99.5 | (S-3) 99.5 |
| | (A) Epoxy compound | | | | | (A-3) 0.5 | | | | | |
| | (B) Isocyanate compound | | | | | | (B-3) 0.5 | | | | |
| | (C) Amine compound | (C-2) 0.5 | | | | | | (C-2) 0.5 | | | |
| | (D) Oxazoline compound | | (D-2) 0.5 | | | | | | (D-2) 0.5 | | |
| | (E) Carbodiimide compound having molecular weight of less than 3,000 | | | (E-2) 0.5 | | | | | | (E-2) 0.5 | |
| | (F) Carboxylic anhydride | | | | (F-2) 0.5 | | | | | | (F-2) 0.5 |

TABLE 1-5-continued

| | | Com. 11 | Com. 12 | Com. 13 | Com. 14 | Com. 15 | Com. 16 | Com. 17 | Com. 18 | Com. 19 | Com. 20 |
|---|---|---|---|---|---|---|---|---|---|---|---|
| Evaluation results | Test Example 1 (Surface smoothness) | D | B | B | B | D | C | B | B | B | B |
| | Test Example 2 (Bending durability) | C | C | C | C | D | D | D | D | D | D |
| | Test Example 3 (Sterilization durability) | D | D | D | D | D | D | D | D | D | D |

Ex.: Example
Com.: Comparative Example

Description of Terms in Tables (T) Polyester Having Naphthalene Structure (T-1) Polyester elastomer having polybutylene naphthalate as structural unit ("PELPRENE EN-5000" (trade name) manufactured by Toyobo Co., Ltd., weight-average molecular weight: 119,000)

(T-2) Polyester elastomer having polybutylene naphthalate as structural unit ("PELPRENE EN-1000" (trade name) manufactured by Toyobo Co., Ltd., weight-average molecular weight: 131,000)

(S) Other Polymer (S-1) Polyester elastomer having polybutylene terephthalate as structural unit ("PELPRENE P-280B" manufactured by Toyobo Co., Ltd., weight-average molecular weight: 128,000)

(S-2) Ether-based polyurethane elastomer ("MIRACTRAN E574PNAT" (trade name) manufactured by Nippon Polyurethane Industry Co., Ltd., weight-average molecular weight: 145,000)

(S-3) Polyamide elastomer ("Pebax 7233" (trade name) manufactured by Arkema Inc., weight-average molecular weight: 48,000)

(A) Epoxy Compound (A-1) Bisphenol A diglycidyl ether ("jER828" (trade name) manufactured by Mitsubishi Chemical Corporation, bifunctional, molecular weight: 340)

(A-2) Glycerol triglycidyl ether ("DENACOL EX-313" (trade name) manufactured by Nagase ChemteX Corporation, trifunctional, molecular weight: 260)

(A-3) Tetraglycidyl diaminodiphenylmethane ("SUMI-EPDXY ELM-434" (trade name) manufactured by Sumitomo Chemical Co., Ltd., tetrafunctional, molecular weight: 423)

(B) Isocyanate Compound (B-1) p-Tolyl isocyanate (reagent, manufactured by Tokyo Chemical Industry Co., Ltd., monofunctional, molecular weight: 133)

(B-2) 1,3-Bis(isocyanatomethyl)benzene ("TAKENATE 500" (trade name) manufactured by Mitsui Chemicals, Inc., bifunctional, molecular weight: 188)

(B-3) 1,3,5-Tris(6-isocyanatohex-1-yl)-1,3,5-triazine-2,4,6 (1H, 3H, 5H)-trione ("CORONATE HX" (trade name) manufactured by Nippon Polyurethane Industry Co., Ltd., trifunctional, molecular weight: 505)

(C) Amine Compound (C-1) 4,4'-Diaminodiphenylmethane (reagent, manufactured by Tokyo Chemical Industry Co., Ltd., bifunctional, molecular weight: 198)

(C-2) 1,3,5-Triazine-2,4,6-triamine (reagent, manufactured by FUJIFILM Wako Pure Chemical Corporation, trifunctional, molecular weight: 126)

(C-3) Tetrakis(4-aminophenyl)methane (reagent, manufactured by Tokyo Chemical Industry Co., Ltd., tetrafunctional, molecular weight: 381)

(D) Oxazoline Compound (D-1) 2,2'-(1,3-Phenylenebis(2-oxazoline) ("1,3-BPO" (trade name) manufactured by Mikuni Pharmaceutical Industrial Co., Ltd., bifunctional, molecular weight: 216)

(D-2) Polymeric oxazoline ("EPOCROS RPS-1005" (trade name) manufactured by Nippon Shokubai Co., Ltd., weight-average molecular weight: 160,000, amount of oxazoline group: 0.27 mmol/g)

(E) Carbodiimide Compound Having Molecular Weight of Less Than 3,000

(E-1) Low-molecular-weight monocarbodiimide ("Stabaxol I" (trade name) manufactured by Rhein Chemie GmbH, molecular weight: 362)

(E-2) Cyclic carbodiimide ("CARBOSISTA TCC-NP" (trade name) manufactured by Teijin Limited, molecular weight: 516)

(F) Carboxylic Anhydride (F-1) 4-Ethynylphthalic anhydride (reagent, manufactured by Tokyo Chemical Industry Co., Ltd., monofunctional, molecular weight: 172)

(F-2) 1,2,4,5-Cyclohexanetetracarboxylic dianhydride (reagent, manufactured by Tokyo Chemical Industry Co., Ltd., bifunctional, molecular weight: 224)

(F-3) 3,3',4,4'-Diphenyl ether tetracarboxylic dianhydride (reagent, manufactured by Tokyo Chemical Industry Co., Ltd., bifunctional, molecular weight: 294) Chain Extender Used in Comparative Example (e-3) Polycarbodiimide ("Stabaxol P100" (trade name) manufactured by Rhein Chemie GmbH, weight-average molecular weight: 15,000)

The results in Table 1 show the following.

In Comparative Example 1, although the cover layer includes a polyester having a naphthalene structure, the polyester is not a chain-extended product specified in the present invention. The flexible tube of Comparative Example 1 was unsatisfactory in terms of bending durability and sterilization durability.

In Comparative Example 2, the cover layer includes a chain-extended product of a polyester having a naphthalene structure, the chain-extended product being prepared using a polycarbodiimide having a weight-average molecular weight of 15,000. The flexible tube of Comparative Example 2 was unsatisfactory in terms of surface smoothness and sterilization durability.

The results of Comparative Examples 3 to 20 show that even when the chain extender specified in the present invention is used, at least the sterilization durability is unsatisfactory unless the polyester chain has a naphthalene structure.

On the other hand, in Examples 1 to 25, the cover layer included a chain-extended product of a polyester having a naphthalene structure specified in the present invention, and all of the surface smoothness, bending durability, and sterilization durability were satisfactory.

The comparison between Examples 10 and 11, the comparison between Examples 12 and 13, and the comparison between Example 14 and Examples 15 and 16 show that the use of a polymeric oxazoline compound, a carbodiimide compound having a ring structure, and a tetracarboxylic dianhydride as the chain extender enables further improvement in the characteristics of the flexible tube for an endoscope. The use of the above chain extender enables gelation of the polyester having a naphthalene structure to be suppressed, which is considered to be one of the factors for improving the characteristics.

The present invention has been described together with embodiments thereof; however, we do not intend to limit our invention in any of the details of the description unless otherwise specified. We believe that the invention should be broadly construed without departing from the spirit and scope of the invention as defined by the appended claims.

REFERENCE SIGNS LIST

2 electronic endoscope (endoscope)
3 insertion section
3*a* flexible tube
3*b* angle portion
3*c* tip portion
5 main-body operation section
6 universal cord
11 spiral tube
11*a* metal strip
12 tubular mesh
13 cap
14 flexible-tube base
15 cover layer

What is claimed is:

1. A flexible tube for an endoscope, the flexible tube comprising:

a sleeve-shaped flexible-tube base having flexibility; and a cover layer covering an outer periphery of the flexible-tube base, wherein the cover layer includes a chain-extended product of a polyester having a naphthalene structure, the chain-extended product includes a constituent component derived from at least one chain extender selected from the group consisting of (A) an epoxy compound, (B) an isocyanate compound, (C) an amine compound, (D) an oxazoline compound, (E) a carbodiimide compound having a molecular weight of less than 3,000, and (F) a carboxylic anhydride and a constituent component derived from a polyester having a naphthalene structure, both the content of the chain-extended product of a polyester having a naphthalene structure in the cover layer when the cover layer is formed of a single layer and the content of the chain-extended product of a polyester having a naphthalene structure in the outermost layer when the cover layer is formed of a plurality of layers are 80% by mass or more, and the constituent component derived from the (A) epoxy compound includes a constituent component derived from a bifunctional to hexafunctional epoxy compound, or the constituent component derived from the (B) isocyanate compound includes a constituent component derived from either a bifunctional or trifunctional isocyanate compound, or the constituent component derived from the (C) amine compound includes a constituent component derived from a bifunctional to tetrafunctional amine compound, or the constituent component derived from the (D) oxazoline compound includes a constituent component derived from either a bisoxazoline compound or a polymeric oxazoline compound, or the constituent component derived from the (E) carbodiimide compound having a molecular weight of less than 3,000 includes a constituent component derived from either a linear mono carbodiimide compound or a compound having a ring including a carbodiimide group as a ring-forming component, a weight-average molecular weight of the compound being from 200 to 2000, or the constituent component derived from the (F) carboxylic anhydride includes a constituent component derived from either dicarboxylic anhydrides or a tetracarboxylic dianhydride.

2. An endoscopic medical device comprising the flexible tube for an endoscope according to claim 1.

3. A method for producing a flexible tube for an endoscope according to claim 1, the method comprising:

forming the cover layer on at least an outer periphery of the sleeve-shaped flexible-tube base having flexibility.

4. A method for producing an endoscopic medical device, the method comprising:

a step of obtaining a flexible tube for an endoscope by the method for producing a flexible tube for an endoscope according to claim 3; and a step of incorporating the obtained flexible tube for an endoscope into an insertion section of an endoscopic medical device.

5. A method for producing an endoscopic medical device, the method comprising:

incorporating the flexible tube for an endoscope according to claim 1 into an insertion section of an endoscopic medical device.

6. The flexible tube for an endoscope according to claim 1, wherein the cover layer is formed of a single layer and the content of the chain-extended product of a polyester having a naphthalene structure in the cover layer is 90% by mass or more.

7. The flexible tube for an endoscope according to claim 1, wherein the constituent component derived from the (B) isocyanate compound is a constituent component derived from a trifunctional isocyanate compound, or the constituent component derived from the (C) amine compound is a constituent component derived from a tetrafunctional amine compound.

* * * * *